US005836881A

United States Patent [19]

Bae

[11] Patent Number: 5,836,881

[45] Date of Patent: Nov. 17, 1998

[54] FOCUSING DELAY CALCULATION METHOD FOR REAL-TIME DIGITAL FOCUSING AND APPARATUS ADOPTING THE SAME

[75] Inventor: Moo-Ho Bae, Seoul, Rep. of Korea

[73] Assignee: Medison Co., Ltd., Rep. of Korea

[21] Appl. No.: 18,007

[22] Filed: Feb. 3, 1998

[30] Foreign Application Priority Data

Feb. 4, 1997 [KR] Rep. of Korea ........................ 97-3418

[51] Int. Cl.[6] ........................................ A61B 8/00

[52] U.S. Cl. ........................................ 600/447

[58] Field of Search .................................... 600/437, 444, 600/447; 367/7, 11, 138; 73/626

[56] References Cited

U.S. PATENT DOCUMENTS 5,581,517 12/1996 Gee et al. ............................... 367/138
5,696,737 12/1997 Hossack et al. ......................... 367/138
5,724,972 3/1998 Petrofsky ................................ 600/437

*Primary Examiner*—George Manuel

*Attorney, Agent, or Firm*—Dilworth & Barrese

[57] ABSTRACT

A focusing delay calculation apparatus for real-time digital focusing calculates focusing delay times for individual array elements constituting an array transducer in an ultrasonic imaging system in which a focal point is varied on the basis of a midpoint algorithm. A delay variable calculator uses a focusing reference distance, integer focusing delay distances and decision variables corresponding to an array element at an n-th focal point to calculate a delay variable corresponding to the array element at an (n+1)th focal point. An updating unit uses the delay variable calculated by the delay variable calculator to produce the integer focusing delay distance and the decision variable corresponding to the array element, and then supplies the produced integer focusing delay distance and decision variable to the delay variable calculator. The delay variable is represented as a value having places below a decimal point. Thus, the present invention can calculate a focusing delay distance represented with accuracy below a decimal point with respect to a varied focal point. and implements the calculation of the focusing delay with the addition of simple hardware, accordingly, the manufacturing cost is low.

10 Claims, 2 Drawing Sheets

FOCUSING DELAY CALCULATION METHOD FOR REAL-TIME DIGITAL FOCUSING AND APPARATUS ADOPTING THE SAME

BACKGROUND OF THE INVENTION

The present invention relates to a focusing delay calculation method for a real-time digital focusing for use in an ultrasonic imaging system, and an apparatus adopting the same.

In case of the ultrasonic reception focusing, distances from a reflection source into which ultrasonic pulses are focused to array elements in a transducer array, are varied. In addition, when a focal point is varied, a variation of the distances between the array elements and the focal point becomes also different from each other. Thus, for a real-time digital reception focusing in an ultrasonic image system, generation of different sampling clock pulses is required with respect to the array elements having each of different distances from the reflection source.

Accordingly, the applicant of this application has proposed a real-time digital reception focusing method and apparatus on the basis of a midpoint algorithm disclosed in an article entitled "An efficient ellipse-drawing algorithm" of Van Aken, J. R. in IEEE Computer Graphics and Application Magazine, vol. 4, no. 9, pp. 24–35, 1984. The digital reception focusing method and apparatus proposed by the applicant determines an integer focusing delay distance in order to generate sampling clock, and generates sampling clock for each array element using the determined integer focusing delay distance. Prior to describing the determination of the integer focusing delay distance, geometrical relationship of the array elements involving with a specific focal point will be described with reference to FIG. 1 as follows.

An array transducer 1 shown in FIG. 1 has a one-dimensional linear array. Each array element 1A is arranged at a certain interval along the horizontal axis. The center of the array transducer 1 is positioned at the origin "O". The reference character "x" is an abscissa from the center of each array element, and θ denotes a steering angle which is generally zero in case of a linear array, r denotes a focusing reference distance between the array element positioned at the center of the array transducer and a focal point P, and l denotes a real-number focusing delay distance with respect to each of remaining array elements.

When a medium in which an ultrasonic wave travels is an un-damped medium having homogeneity, using the definitions relevant to FIG. 1, a focusing delay time of each array element is represented as a time when it takes an ultrasonic wave to travel, by a distance l expressed as the following equation (1), $$l=(r^2+\alpha r+\beta)^{1/2}-r \quad (1)$$

In above equation (1), $\alpha=2x\sin\theta$ and $\beta=x^2$. r is varied according to the distance up to a reflection source (not shown), and θ is not varied with respect to a scanning line. Also, x has a constant value with respect to a given array element. Thus, if a real number l satisfying equation (1) with respect to the given r can be obtained, a focusing delay time can be obtained. Accordingly, sampling clock with respect to corresponding array transducer.

In equation (1), r is moved to the other side and then both sides are squared, a function f(r, l) expressed as the following equation (2) can be obtained.

$$f(r,\ l)=l^2+2lr-\alpha r-\beta=0 \quad (2)$$

In equation (2), when all coefficients are integer, and r and l satisfy a condition expressed as the following inequality (3), the ultrasonic imaging system can use a midpoint algorithm for calculation of the focusing delay distance.

$$-1\leq dl/dr\leq 0 \quad (3)$$

Referring to FIG. 2, a process of selecting the next point using a midpoint algorithm is described. In FIG. 2, when two curves expressed as solid lines indicate continuous curves of the two cases requiring approximation, assuming that a point $A(x_n,\ y_n)$ shown in FIG. 2 is selected at the n-th drawing stage, a point at the (n+1)th drawing stage becomes either $B(x_{n+1},\ y_n)$ or $D(x_{n+1},\ y_n-1)$. A decision variable $d_n$ is used for determining one of the two finally. If a value of the decision variable $d_n$ is greater than 0, it is determined that the curve becomes closer to $D(x_{n+1},\ y_n-1)$, while if the value of $d_n$ is smaller than 0, it is determined that the curve becomes closer to $B(x_{n+1},\ y_n)$. Such a decision variable $d_n$ is defined as the following equation (4) using the same notations as used in the equation (2).

$$d_n=4.f(r_{n+1},\ i_n-0.5) \quad (4)$$

Here, $i_n$ is an integer being closest to $l_n$ satisfying $f(r_n,\ l_n)$. Therefore, when the value of the decision variable $d_n$ can be known, the value of $d_{n+1}$, the (n+1)th integer focusing delay distance $i_{n+1}$ and the focusing reference distance $r_{n+1}$ can be decided on a geometrically two-dimensional plane in which unit distances relevant to r and i are defined. Thus, a focusing delay distance can be calculated with respect to the varying focusing distance on a real-time basis.

However, in the case that it is desired to obtain a more precise integer focusing delay distance i, a unit distance must be short. For doing so actually, a clock frequency should be heightened as much as the shortened unit distance. Consequently, high-speed hardware is required. When high-speed hardware is not supposed to use, the i-axis or l-axis should be different from the r-axis in scale. That is, the i-axis should be designed densely and the r-axis should be designed sparsely. However, in this case, when the unit distance of r is small, it becomes more difficult to satisfy the condition expressed as equation (3).

SUMMARY OF THE INVENTION

To solve the above problems, it is an object of the present invention to provide a method and apparatus which can obtain a more precise focusing delay.

To accomplish the above object of the present invention, there is provided a method for calculating a focusing delay distance for each of array elements constituting an array transducer in an ultrasonic imaging system in which a focal point is varied on the basis of a midpoint algorithm, the method comprising the steps of:

(a) calculating a delay variable corresponding to each array element at an (n+1)th focal point, using a focusing reference distance, an integer focusing delay distance and a decision variable which correspond to the each array element at an n-th focal point;

(b) calculating the focusing reference distance, the integer focusing delay distance and the decision variable corresponding to the each array element at the (n+1)th focal point, using the delay variable in step (a); and (c) producing an focusing delay distance corresponding to the each array clement at the (n+1)th focal point, by adding the delay variable calculated in step (a) and the integer focusing delay distance calculated in step (b).

There is also provided an apparatus for calculating a focusing delay distance for each of array elements constituting an array transducer in an ultrasonic imaging system in which a focal point is varied on the basis of a midpoint algorithm, the apparatus comprising:

delay variable calculation means for calculating delay variable corresponding to each array element at an (n+1)th focal point, using a focusing reference distance, integer focusing delay distances and decision variables corresponding to the each array element at an n-th focal point; and updating means for producing the integer focusing delay distance and the decision variable corresponding to the each array element at the (n+1)th focal point, using the delay variable calculated by the delay variable calculation means, and supplying the produced integer focusing delay distance and decision variable to the delay variable calculation means.

BRIEF DESCRIPTION OF THE DRAWINGS

The preferred embodiments are described with reference to the drawings wherein.

DETAILED DESCRIPTION OF THE PREFERRED EMBODIMENT

A preferred embodiment of the present invention will be described in detail with reference to the accompanying drawings.

The present invention is basically to obtain i to make $d_n$ further closer to '0'. In other words, a delay variable $e_n$ satisfying the following equation (5) is simply calculated on a real-time basis, in order to obtain an (n+1)th integer focusing delay distance.

$$4f(r_{n+1}, i_n+e_n)=0 \tag{5}$$

Since an exact $e_n$ cannot be simply calculated, an approximation value of $e_n$ is obtained according to the following procedure in actuality. First, the following equation (5) is primarily differentiated and then linearly approximated, to obtain the following equation (6).

$$0 = 4f(r_{n+1}, i_n + e_n) \approx 4f(r_{n+1}, i_n) + 4\frac{\partial f}{\partial i_n} e_n \approx d_n + \frac{\partial f}{\partial i_n} e_n \tag{6}$$

Here, $r_{n-1}$ is obtained by adding an integer and $r_n$, and the following equation (7) is established.

$$4\frac{\partial f}{\partial i_n} = 8i_n + 8r_n + 4 \tag{7}$$

As a result, a delay variable $e_n$ is expressed as the following equation $$e_n = \frac{-d_n}{8(i_n + r_n + 1/2)} \tag{8}$$

Using the equation (8), an accurate $i_{n+1}$ down to three or more places of a decimal point is generally obtained. When u>10, $i_{n+1}$ having one or more places on the right of a decimal point is obtained even when $r_n$ is small. Here, an inequality u>10 means that a unit distance u is greater than 10, in which the unit distance is given to a distance travelled by an ultrasonic wave during a one-period of master clock. For example, when a master clock frequency is 50 MHz, a unit distance is about 0.03 mm underwater and thus satisfying u>0.3 mm is sufficient.

Further advantageously, a general division of an integer needs a considerable complexity in hardware. However, in equation (8), a quotient of the division is pre-defined within ±0.5 and only the quotient of 2~3 bits being a word length of a desired accuracy is calculated. Thus, a division operation can be accomplished by a smaller number of adders and registers.

Figure 1:
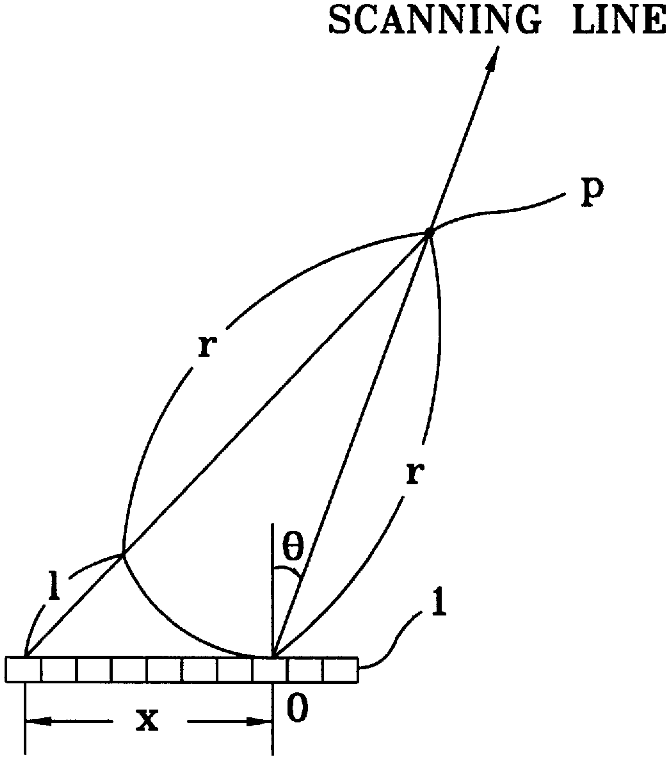
FIG. 1 is a geometrically conceptual diagram for explaining a focusing delay with respect to individual array elements in an array transducer.
Figure 2:
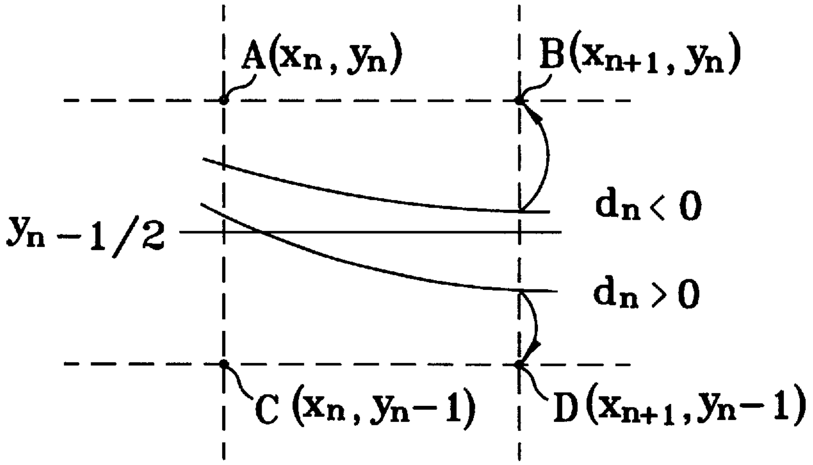
FIG. 2 is a view for explaining the selection of the next [another] point using a decision variable of a midpoint algorithm.
Figure 3:
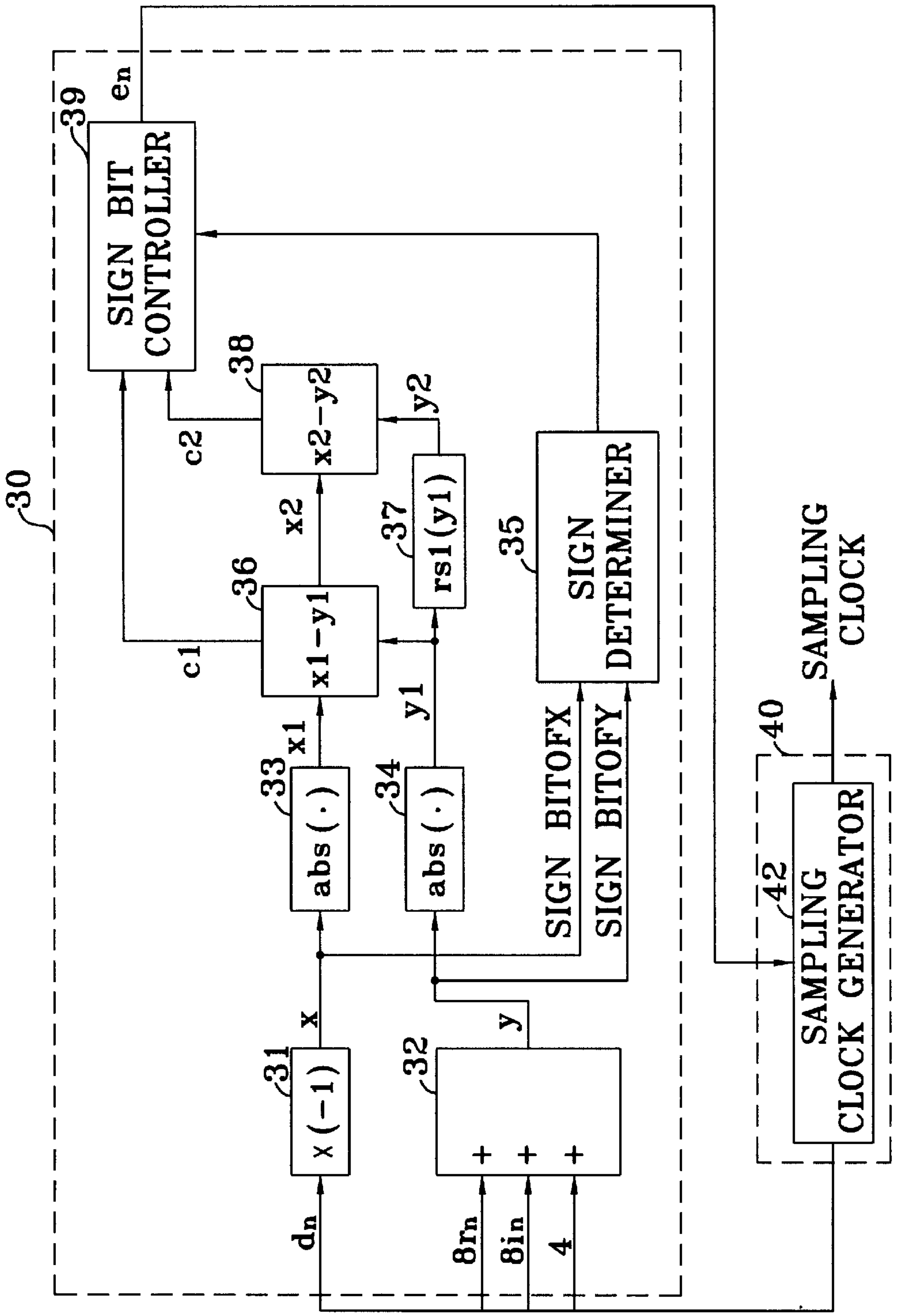
FIG. 3 is a block diagram showing a varying sampling clock generator according to a preferred embodiment of the present invention.

FIG. 3 is a block diagram showing a varying sampling clock generator according to a preferred embodiment of the present invention. In FIG. 3, a delay variable calculator 30 uses a focusing reference distance, an integer focusing delay distance and a decision variable corresponding to an array element at an n-th focal point, to calculate a delay variable corresponding to the array element at an (n+1)th focal point. An updating unit 40 uses the delay variable $e_n$ calculated by the delay variable calculator 30 to calculate an integer focusing delay distance $i_{n+1}$ and a decision variable $d_{n+1}$ corresponding to the array elements at an (n+1)th focal point. More specifically, the updating unit 40 adds the delay variable $e_n$ received from the delay variable calculator 30 and an integer focusing delay distance $i_n$ stored in internal memory (not shown), to then produce an integer focusing delay distance $i_{n+1}$ corresponding to the array element at the (n+1)th focal point, and calculates the corresponding decision variable $d_{n+1}$ at the (n+1)th focal point using the equation (8). The focusing reference distance $r_{n+1}$ is produced by adding the n-th focusing reference distance $r_n$ and an integer. The focusing reference distance $r_{n+1}$, the integer focusing delay distance $i_{n+1}$ and the decision variable $d_{n+1}$ corresponding to the (n+1)th focal point are supplied to the delay variable calculator 30 so that the delay variable corresponding to the array element at an (n+2)th focal point is calculated.

The updating unit 40 includes a sampling clock generator 42 for generating sampling clock to acquire an ultrasonic wave signal from the (n+1)th focal point of the corresponding array element. The sampling clock generator 42 generates sampling clock for acquiring an ultrasonic wave signal from the (n+1)th focal point at the time delayed by a time corresponding to the focusing delay distance being the added result of the delay variable $e_n$ and integer focusing delay distance $i_{n+1}$ at the (n+1)th focal point from a time corresponding to the n-th focal point.

A calculation procedure of the delay variable $e_n$ used in calculation of the focusing delay distance corresponding to the (n+1)th focal point will be described below in more detail.

The $d_n$, $r_n$, and $i_n$ input to the delay variable calculator 30 are constructed with an N-bit word, respectively and N-bit is generally sufficient as 20 bits. Thus, N-bit adders, multiplexers and registers are needed to calculate the input variables. A multiplier 31 embodied by an N-bit adder inverts the sign of an input n-th decision variable $d_n$ and outputs the sign-inverted data x. The data x is supplied to a first absolute value calculator 33 and the sign bit of the data x is supplied to a sign determiner 35. An operator 32 embodied by two N-bit adders outputs data y which results from $8r_n+8i_n+4$ with respect to the input $r_n$, $i_n$, and 4. The data y is supplied to a second absolute value calculator 34 and the sign bit of the data y is supplied to the sign determiner 35.

The first absolute value calculator 33 which is embodied with an N-bit adder and an N-bit multiplexer, calculates an absolute value x1 of the data x received from the multiplier 31. The absolute value x1 is output to a first subtracter 36. A second absolute value calculator 34 which is embodied with an N-bit adder and an N-bit multiplexer calculates an absolute value y1 of the data y received from the operator 32. The absolute value y1 is output to the first subtracter 36 and a shifter 37.

Meanwhile, the sign determiner 35 which is embodied with a single exclusive OR gate having one-bit output, receives the sign bits of the data x and y output from the multiplier 31 and the operator 32 and produces data Q_SIGN from the received sign bits. The data Q_SIGN is supplied to a sign controller 39. The first subtracter 36 subtracts the absolute value y1 of the second absolute value calculator 34 from the absolute value x1 of the first absolute value calculator 33, and outputs the resultant carry bit c1 and subtracted result x2 to the sign controller 39 and a second subtracter 38, respectively. The shifter 37 shifts the absolute value y1 supplied from the second absolute value calculator 34 by a one-bit to the right, and supplies the resultant data y2 to the second subtracter 38. The second subtracter 38 subtracts the data x2 output from the first subtracter 36 by the data y2 supplied from the shifter 37, and supplies the resultant carry bit c2 to the sign controller 39.

The sign controller 39 which is embodied with a two-bit adder and a two-bit multiplexer, produces a two--bit data having the carry bit c1 as a most significant bit (MSB) and the carry bit c2 as a least significant bit (LSB). The sign controller 39 uses the data Q_SIGN supplied from the sign determiner 35 as a sign of the two-bit data constituted with the carry bits c1 and c2. Therefore, the delay variable $e_n$ that is finally output from the sign controller 39 is a three--bit data constituted with the carry bits c1 and c2 and the data Q_SIGN as a sign bit.

The delay variable $e_n$ output from the delay variable calculator 30 is supplied to the updating unit 40, and is used for generation of sampling clock for an (n+1)th focal point.

Meanwhile, when a calculation speed of the delay variable should be considerably fast, a pipelined register is used to perform a pipeline operation.

The FIG. 3 embodiment has been described to calculate the delay variable for a single array element. However, it is apparent to a person skilled in the art that the above description can be applied to the other array elements constituting an array transducer.

The above-described embodiment has been described with respect to generation of the sampling clock. However, various modifications and variations are possible as described below.

An integer focusing delay distance and a corresponding delay variable can be used as a control signal for delay taps to delay an ultrasonic wave signal received from a general analog beam former on an analog basis.

U.S. Pat. No. 5,345,426 entitled "Delay interpolator for digital phased array ultrasound beamformers", which issued on Sep. 6, 1994, discloses technique that coarsely samples an ultrasonic wave signal received via each channel, and then produces data to be used for imaging through interpolation. The delay variable and the corresponding integer focusing delay distance calculated according to the present invention can be used for determination of a data set to be used for interpolation. It is possible to use the delay variable in determination of an interpolation coefficient.

Referring to a paper entitled "Electronic scanner for a phased-array ultrasound transducer" by Ronald D. Gatzke, James T. Fearnside, and Sydney M. Karp, disclosed in Hewlett Packard Journal Vol. 34, No. 12, pp. 13–20, December 1983, a delay variable and a corresponding integer focusing delay distance according to the present invention can be used for rotation of a phase of a radio-frequency (RF) signal. This uses the fact that a RF envelop is not much varied for a one-sample interval.

As described above, the method and apparatus according to the present invention can obtain a focusing delay distance represented with accuracy below a decimal point with respect to a varying focal point. Accordingly, calculation of a focusing delay distance represented with accuracy below a decimal point can be realized with the addition of simple hardware, and thus, the manufacturing cost is low.

While only certain embodiments of the invention have been specifically described herein, it will be apparent that numerous modifications may be made thereto without departing from the spirit and scope of the invention.

What is claimed is:

1. A method for calculating a focusing delay distance for each of a plurality of array elements constituting an array transducer in an ultrasonic imaging system in which a focal point is varied on the basis of a midpoint algorithm, the method comprising the steps of:

(a) calculating a delay variable corresponding to each array element at an (n+1)th focal point, using a focusing reference distance, an integer focusing delay distance and a decision variable which correspond to said each array element at an n-th focal point;

(b) calculating the focusing reference distance, the integer focusing delay distance and the decision variable corresponding to said each array element at the (n+1)th focal point, using the delay variable in step (a); and (c) producing the focusing delay distance corresponding to said each array element at the (n+1)th focal point, by adding the delay variable calculated in step (a) and the integer focusing delay distance calculated in step (b).

2. The method according to claim 1, wherein the delay variable is represented as a value having places below a decimal point.

3. The method according to claim 2, wherein the delay variable $e_n$ corresponding to an array element of the (n+1)th focal point is $$e_n = -d_n / \{8(i_n + r_n + ½)\},$$

where $d_n$, $i_n$ and $r_n$ are the decision variable, the integer focusing delay distance and the focusing reference distance corresponding to said each array element at the n-th focal point, respectively.

4. The method according to claim 1, wherein the actual focusing delay distance obtained in said step (c) is used for generation of sampling clock to acquire an ultrasonic wave signal from the (n+1)th focal point of the corresponding array element.

5. The method according to claim 1, wherein the focusing delay distance obtained in step (c) is used to control the delay of the ultrasonic wave signal received from an analog beam former on an analog basis.

6. An apparatus for calculating a focusing delay distance for each of a plurality of array elements constituting an array transducer in an ultrasonic imaging system in which a focal point is varied on the basis of a midpoint algorithm, the apparatus comprising:

delay variable calculation means for calculating a delay variable corresponding to each array element at an (n+1)th focal point, using a focusing reference distance, an integer focusing delay distance and a decision variable corresponding to said each array element at an n-th focal point; and updating means for producing the integer focusing delay distance and the decision variable corresponding to said each array element at the (n+1)th focal point, using the delay variable calculated by the delay variable calculation means, and supplying the produced integer focusing delay distance and the decision variable to the delay variable calculation means.

7. The apparatus according to claim 6, wherein the delay variable is represented as a value having places below a decimal point.

8. The according to claim 7, wherein the delay variable $e_n$ corresponding to an array element of said (n+1)th focal point is $$e_n=-d_n/\{8(i_n+r_n+1/2)\}.$$

where $d_n$, $i_n$ and $r_n$ are the decision variable, the integer focusing delay distance and the focusing reference distance corresponding to said particular array element at the n-th focal point, respectively.

9. The apparatus according to claim 6, wherein said updating means comprises a sampling clock generator for generating sampling clock to acquire an ultrasonic wave signal from the (n+1)th focal point of the corresponding array element, using the delay variable calculated by said delay variable calculation means.

10. The apparatus according to claim 9, wherein said sampling clock generator generates sampling clock for a corresponding array element based on addition of the delay variable and the corresponding integer focusing delay distance.

* * * * *